(12) United States Patent
Steadman Booker et al.

(10) Patent No.: US 11,178,346 B2
(45) Date of Patent: Nov. 16, 2021

(54) CHARGE SHARING CALIBRATION METHOD AND SYSTEM

(71) Applicant: KONINKLIJKE PHILIPS N.V., Eindhoven (NL)

(72) Inventors: Roger Steadman Booker, Aachen (DE); Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/960,787

(22) PCT Filed: Jan. 8, 2019

(86) PCT No.: PCT/EP2019/050323
§ 371 (c)(1),
(2) Date: Jul. 8, 2020

(87) PCT Pub. No.: WO2019/137901
PCT Pub. Date: Jul. 18, 2019

(65) Prior Publication Data
US 2021/0067710 A1   Mar. 4, 2021

(30) Foreign Application Priority Data
Jan. 9, 2018 (EP) .................................... 18150759

(51) Int. Cl.
*H04N 5/32* (2006.01)
*A61B 6/00* (2006.01)
*G01N 23/046* (2018.01)

(52) U.S. Cl.
CPC ............... *H04N 5/32* (2013.01); *A61B 6/482* (2013.01); *G01N 23/046* (2013.01)

(58) Field of Classification Search
CPC ......... H04N 5/32; A61B 6/482; H01N 23/046
See application file for complete search history.

(56) References Cited

U.S. PATENT DOCUMENTS

| | | | | |
|---|---|---|---|---|
| 5,214,581 A | * | 5/1993 | Rhodes | ................... G03H 5/00 378/7 |
| 6,002,741 A | * | 12/1999 | Eisen | ................... G01T 1/2928 378/62 |
| 7,208,739 B1 | * | 4/2007 | Yanoff | ................... G01T 1/171 250/363.09 |

(Continued)

FOREIGN PATENT DOCUMENTS

EP       3109676 A1       12/2016

OTHER PUBLICATIONS

PCT International Search Report, International Application No. PCT/EP2019/050323, Mar. 19, 2019.

(Continued)

*Primary Examiner* — Blake C Riddick
(74) *Attorney, Agent, or Firm* — Larry Liberchuk

(57) ABSTRACT

A signal processing system (SPS) and related method. The system comprises an input interface (IN) for receiving at least two data sets, comprising a first data set and second data set. The first data set is generated by an X-ray detector sub-system (XDS) at a first pixel size and the second data set generated at a second pixel size different from the first pixel size. An estimator (EST) is configured to compute, based on the two data sets, an estimate of a charge sharing impact.

6 Claims, 7 Drawing Sheets

(56) References Cited

U.S. PATENT DOCUMENTS

| | | | |
|---|---|---|---|
| 9,482,764 B1 | 11/2016 | Shahar | |
| 10,365,380 B2 | 7/2019 | Booker | |
| 10,481,285 B1* | 11/2019 | Shahar | G01T 1/244 |
| 2008/0042070 A1* | 2/2008 | Levin | H04N 5/32 |
| | | | 250/370.13 |
| 2011/0036988 A1* | 2/2011 | Campbell | H01L 27/14676 |
| | | | 250/370.07 |
| 2011/0210262 A1* | 9/2011 | Prendergast | G01T 1/247 |
| | | | 250/394 |
| 2012/0104262 A1* | 5/2012 | Wiegert | G01N 23/046 |
| | | | 250/363.03 |
| 2014/0236523 A1* | 8/2014 | Matsushita | G01N 23/087 |
| | | | 702/104 |
| 2015/0139390 A1* | 5/2015 | Bellazzini | G01T 1/17 |
| | | | 378/62 |
| 2015/0369929 A1* | 12/2015 | Durst | G01T 1/2018 |
| | | | 250/362 |
| 2016/0076935 A1* | 3/2016 | Daerr | G01J 1/44 |
| | | | 250/214 R |
| 2016/0377748 A1* | 12/2016 | Sakumura | G01T 7/005 |
| | | | 378/207 |
| 2016/0377749 A1* | 12/2016 | Matsushita | G01T 1/17 |
| | | | 378/207 |
| 2017/0016998 A1* | 1/2017 | Shahar | G01T 1/24 |
| 2017/0322319 A1 | 11/2017 | Iniewski | |
| 2017/0357013 A1* | 12/2017 | Roessl | G01T 1/241 |
| 2018/0192977 A1* | 7/2018 | Jin | A61B 6/585 |
| 2018/0196149 A1 | 7/2018 | Blevis | |
| 2018/0203132 A1* | 7/2018 | Sakumura | G01T 1/16 |
| 2018/0224564 A1* | 8/2018 | Fu | G01T 1/2928 |
| 2018/0252821 A1* | 9/2018 | Svensson | G01T 1/24 |
| 2018/0259657 A1* | 9/2018 | Fu | G01T 7/005 |
| 2018/0317869 A1* | 11/2018 | Rui | A61B 6/585 |
| 2018/0329086 A1 | 11/2018 | Roessl | |
| 2018/0364373 A1* | 12/2018 | Hondongwa | G01T 1/17 |
| 2019/0117172 A1* | 4/2019 | Chang | A61B 6/032 |
| 2020/0249179 A1* | 8/2020 | Yamakawa | G01T 1/36 |

OTHER PUBLICATIONS

Kraft P. et al., "Performance of Single-Photon-Counting PILATUS Detector Modules", Journal of Synchrotron Radiation, Wiley-Blackwell Munksgaard, DK, vol. 16, No. 3, May 1, 2009 (May 1, 2009), pp. 368-375, XP002632471.

Rajbhandary P.L. et al., Effect of Spatio-Energy Correlation in PCD Due to Charge Sharing, Scatter, and Secondary Photons, Progress in Biomedical Optics and Imaging, SPIE—International Society FDR Optical Engineering, Bellingham, WA, US, vol. 10132, Mar. 3, 2017 (Mar. 3, 2017), p. 101320V-101320V, XP060087547.

* cited by examiner

CHARGE SHARING CALIBRATION METHOD AND SYSTEM

FIELD OF THE INVENTION

The invention relates to a signal processing system, to a signal processing method, to an imaging arrangement, to a computer program element and to a computer readable medium.

BACKGROUND OF THE INVENTION

Some X-ray imaging apparatuses, such as computed tomography (CT) scanners, radiography apparatuses or others, use energy discriminating detector equipment. Unlike more traditional detectors that are merely energy integrating, energy discriminating detector systems are capable to analyze the energy spectrum of the X-radiation. This additional information extraction allows for instance spectral imaging to learn about the material composition of the imaged sample.

One type of such energy discriminating detector systems are direct conversion photon counting detectors. These use largely unstructured semiconductors for conversion of X-radiation into detector signals. Structuring or "pixilation" is achieved by arranging a plurality of electrodes on the semiconductor. The electrodes register photon events that are caused by charge clouds formed within the semiconductors due to impacting photons. The electrodes provide the detector signals in form of electrical pulses that can be processed into spectral image data.

An undesirable phenomenon of "charge sharing" may occur in these type of detector or similar event counters. "Charge sharing" is an effect where the very same photon event is registered by more than one of the electrodes and this may disturb the energy discrimination capability of the imaging apparatus.

One way of reducing the influence of charge sharing is to use algorithms that analyze the detected signals of different pixels. In case of a charge sharing event many pulses with a small pulse height are detected at the same instance of time in adjacent pixels. The pulse heights can be combined to recover the initial pulse height.

SUMMARY OF THE INVENTION

There may be a need for alternative ways to improve event counting based imaging.

The object of the present invention is solved by the subject matter of the independent claims where further embodiments are incorporated in the dependent claims. It should be noted that the following described aspects equally apply to the imaging module, and to the imaging apparatus.

According to a first aspect of the invention there is provided a signal processing system, comprising:

an input interface for receiving at least two data sets, comprising a first data set and second data set, the first data set generated by an X-ray detector sub-system at a first pixel size and the second data set generated at a second pixel size different from the first pixel size;

an estimator configured to compute, based on the two data sets, an estimate of a charge sharing impact.

In other words, the pixel size may be changed and the data sets represent measurement for each of the at least two pixel sizes. These measurements are then processed to assess the charge sharing impact in the given detector subsystem.

More specifically, and according to one embodiment, the detector sub-system has a native pixel size and wherein one of the first and second pixel size is the native pixel size and/or wherein at least one of the second and first pixel size is a multiple of the said pixel size.

The pixel size (or area), sometimes expressed in terms of pitch, represents the effective area through which measurements are collected and combined together, eg from a group of native pixels. Specifically, the group of detector pixels are combined or binned into a single readout channel.

More specifically, and in one embodiment, the data sets are obtained by operation of a combiner (which may be part of the system). The combiner is configured to combine the signals generated at the detector sub-system in response to X-radiation exposure, to obtain at least the first or second data set.

According to one embodiment, the combiner includes binning circuitry to bin the signals generated at the X-ray detector sub-system. Other summing circuitry may also be used instead or in combination.

According to one embodiment, the estimator is configured to form one or more ratios based on values as per the first and second data set to obtain said estimate.

According to one embodiment, the system comprises a corrector configured to charge sharing correct, based on the estimate, a third data set generated by the detector-subsystem or by another detector. The third data set is collected in an imaging phase where the signals in the third data set are collected in respect of an object to be imaged, as opposed to the first and second data sets that are together collected earlier as calibration data in a calibration phase prior to the imaging phase.

According to one embodiment, the detector sub-system is of the energy resolving type (or photon counting) type.

According to a second aspect of the invention there is provided an imaging arrangement comprising i) the signal processing system as per any one of the above mentioned embodiments and ii) an X-ray imaging apparatus having the detector sub-system. The X-ray imaging apparatus may be rotational such as a CT scanner or a C-arm system bit other systems as such projective radiography system are not excluded herein.

According to a third aspect of the invention there is provided a signal processing method, comprising:

receiving at least two data sets, comprising a first data set and second data set, the first data set generated by an X-ray detector sub-system at a first pixel size and the second data generated at a second pixel size different from the first pixel size;

computing, based on the two data sets, an estimate of a charge sharing impact.

According to one embodiment, the method comprises:

based on the estimate, correcting, for charge sharing impact, a third data set generated by the detector sub-system or by another detector sub-system.

According to a fourth aspect of the invention there is provided a computer program element, which, when being executed by at least one (data) processing unit, is adapted to cause the processing unit to perform the method as per any one of the mentioned aspects or embodiments.

According to a fifth aspect of the invention there is provided a computer readable medium having stored thereon the program element.

The proposed system and method allows supporting imaging with very small pixel sizes as used in particular in energy-resolving photon counting detectors that are required to cope with very high X-ray flux. Reducing the pixel size is however constrained by the negative impact of charge sharing, which compromises energy performance. Pixel size is therefore chosen to balance the needs in flux capabilities and energy resolution.

The proposed system affords high rate capability at high flux.

The proposed charge sharing compensation system may be implemented in software configured to process calibration data (the above mentioned first and second data sets) obtained at different detector pixel configurations. The readout electronics may be adapted by integrating the above mentioned combiner so as to allow taking calibration data at two or more effective pixel sizes. The calibration data at large equivalent pixel size/pitch can be used to estimate the impact of charge sharing in separate sets of calibration data obtained with smaller pixel pitches. This analysis of the calibration data allows to formulate correction data to compensate charge sharing on projection/image data acquired using the nominal small pixel pitch that may be required to serve all clinically relevant protocols.

BRIEF DESCRIPTION OF THE DRAWINGS

Exemplary embodiments of the invention will now be described with reference to the following drawings (which are not to scale) wherein.

DETAILED DESCRIPTION OF EMBODIMENTS

Figure 1:
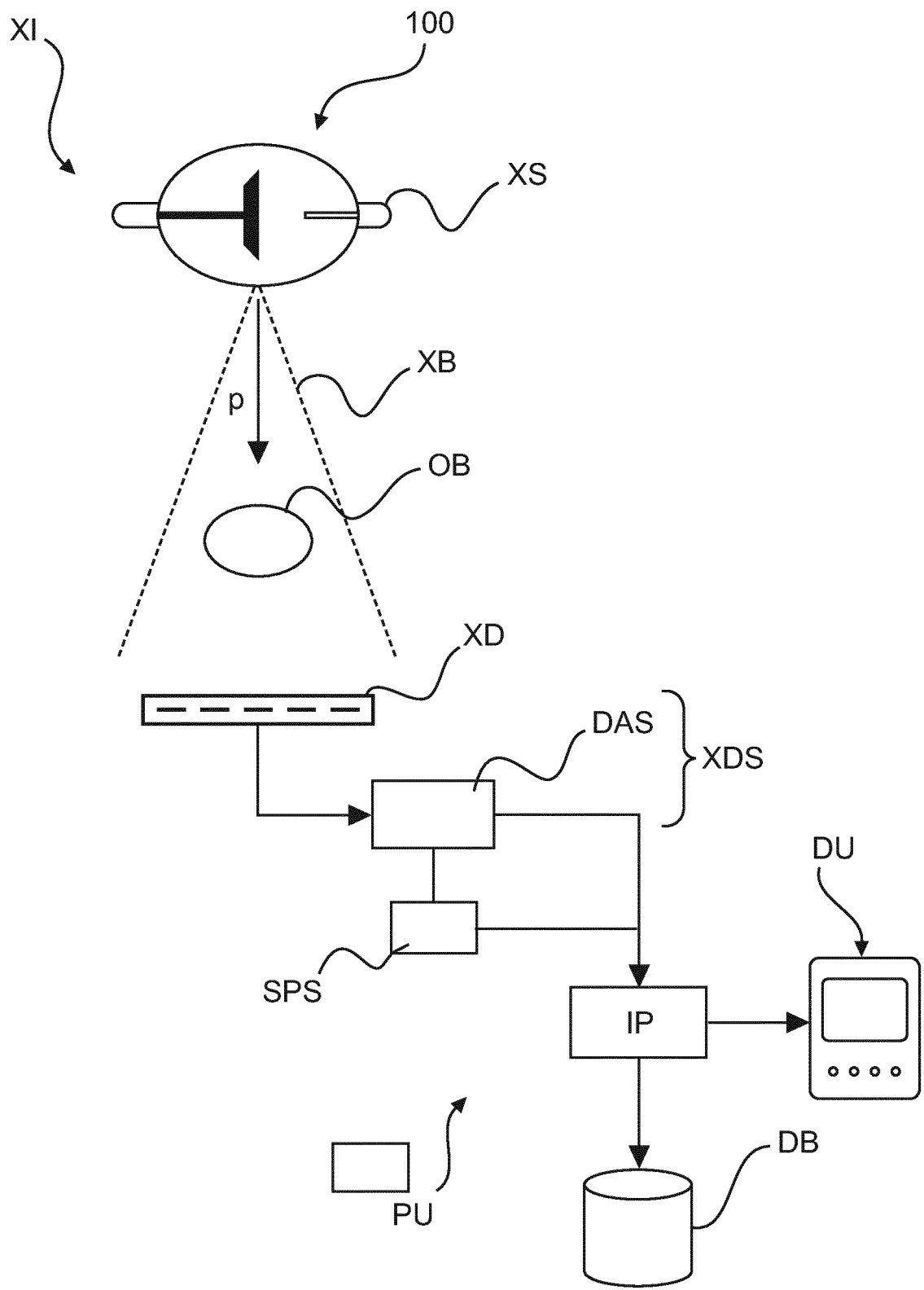
FIG. 1 shows a schematic block diagram of an X-ray imaging arrangement.

With reference to FIG. 1, there is shown a schematic block diagram of an X-ray imaging arrangement 100 including an X-ray imaging apparatus XI (also referred to herein as the "imager"), such as a Computed Tomography apparatus, projection radiography, etc.

The imager XI is configured to produce imagery, in particular in relation to an internal structure and/or material composition of an object OB. The object OB may be animate or inanimate. In particular, the object is a human or animal patient or a part thereof.

The X-ray imager XI is particularly envisaged for, preferably, spectral or photon counting (energy resolving) imaging in the medical field but other applications in non-medical fields are not excluded herein, such as baggage scanning or non-destructive material testing (NDT), etc.

The X-ray imaging apparatus XI includes an X-ray source XS configured to emit X-radiation.

At a distance from the X-ray source XS, across an examination region, there is arranged an X-ray sensitive detector module XD. The X-ray sensitive detector module XD is coupled to data acquisition circuitry DAS. The X-ray sensitive detector module XD and the data acquisition circuitry DAS form together an X-ray detector (sub-)system XDS of the imaging arrangement 100. The module and the DAS may be integrated in one unit or may be arranged discretely and separately but communicatively coupled.

The detector module XD is a transducer that converts X-radiation into electrical signals which are then processed (in manner to be described in more detail below) by the data acquisition circuitry DAS (referred to herein simply as "DAS") into numbers (detector signals). The detector signals may be processed by an image processor IP into the required imagery. Depending on the quantity or contrast one wishes to image for, the image processor implements suitable image processing algorithms such as filtered back-projection (for 3D imagery), phase contrast reconstruction, dark-field reconstruction, transmission reconstruction or any combination thereof. The imagery may be rendered for display on a display device DU (such as monitor) or may be otherwise further processed, or may be stored in a memory DB.

During imaging, the object OB (or a part thereof) to be imaged resides in the examination region between the X-ray source XS and the X-ray detector XD. The X-ray source XS is energized by a user through a control unit (not shown). The X-ray source XS then emits X-radiation in the form of an X-ray beam XB that traverses the examination region and the object Ob to be imaged. The X-ray beam is made up from photons of different energy defined by the spectrum of the X-radiation generated by the X-ray source XS.

The X-photons interact with matter in the object OB. For instance, some of the photons are absorbed by the matter whereas other photons emerge at the far side of the object (as viewed from the X-ray source), and then interact with the X-ray sensitive detector XD. Some of the photons that emerge at the far side of the object OB have been scattered because of their interaction with the matter in the object OB whilst other photons emerge unscattered. An anti-scatter grid (not shown) may be used to prevent scattered photons to reach the detector system to improve image quality.

Each photon in the X-ray beam has a certain energy. The X-ray imager XI as mainly envisaged herein is capable of event counting to quantify the manner in which the photons interact with the detector module XD. In one particular embodiment the X-ray imager is a spectral imager that allows spectral analysis of the detected X-radiation/photons. This capability allows for instance a material decomposition of the object. That is, the detected radiation can be analyzed to identify different types of material tissue in the object for instance.

More specifically, the photons, after interaction with the object OB, interact with an X-ray sensitive layer of the X-ray detector XD that cause the electrical signals which are then picked up and processed within the DAS.

The imaging arrangement 100 as proposed herein includes a novel signal processing system SPS that is configured to correct the detector signals for charge sharing effects that take place in the detector system XDS. Charge sharing is an effect that corrupts fidelity of the detector signals. If uncounted for, charge sharing may undermine image quality and spectral separation.

Figure 2:
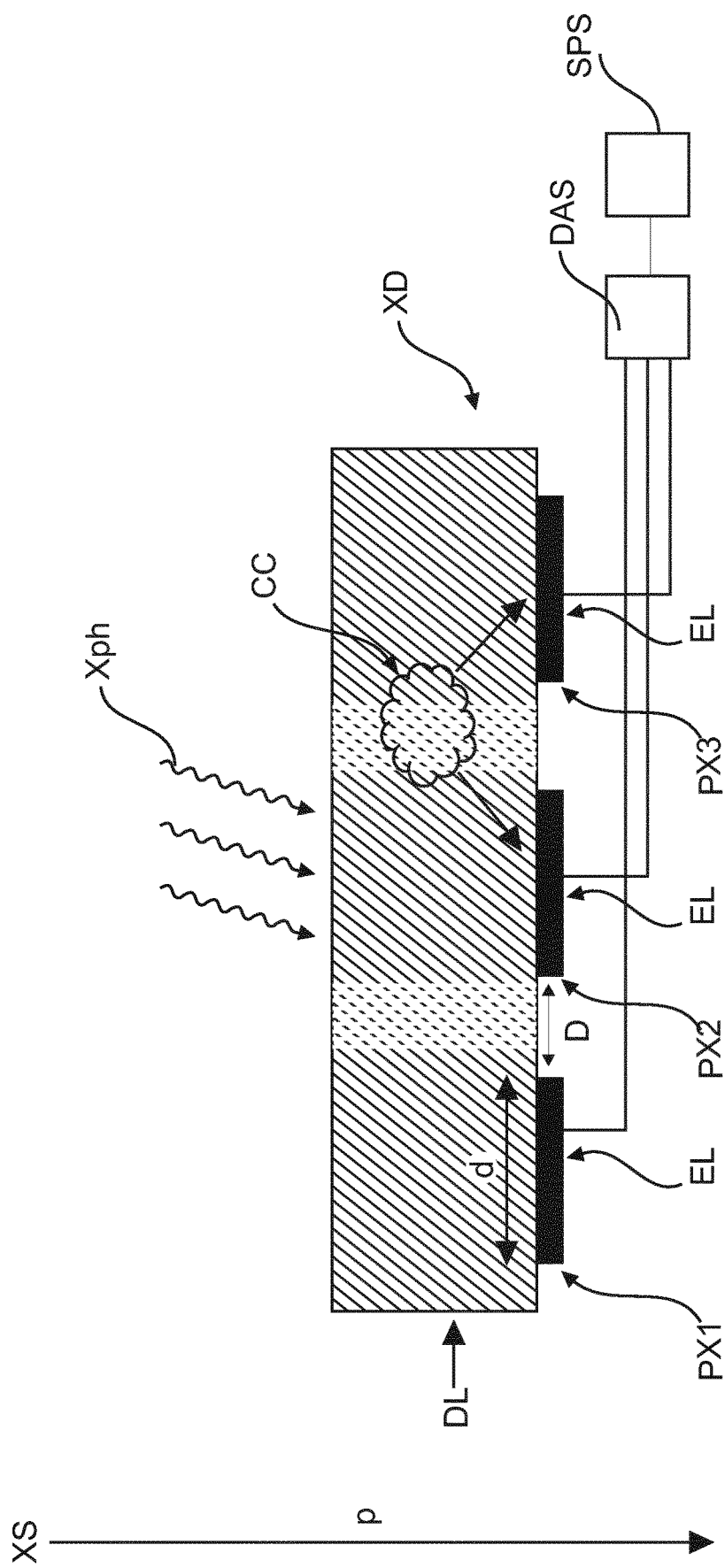
FIG. 2 shows a sectional view of an X-ray detector module with an X-radiation component.

Before turning to operation of the newly proposed signal processing system SPS, reference is first made to FIG. 2 to explain the charge sharing effect in more detail. FIG. 2, shows a sectional view through the detector sub-system XDS, in particular the X-ray module XD and parts of the DAS. The section plane is parallel to the main propagation direction p of the X-radiation XB (see FIG. 1).

The detector module XD is preferably of the direct convertor type. More particularly, the detector XD includes, as the X-ray radiation sensitive component, a direct conversion layer DL. The direct conversion layer DL is formed from a suitable semiconductor. The semiconductors have a crystalline structure, such as Silicon, CdTe, CZT, GaAs and Ge, and others. Just like the whole of the detector XD unit, the conversion layer DL is generally of a rectangular shape and forms an array. In the view of FIG. 2, the layer's other length dimension extends into the paper plane of the Figure. The direct conversion layer DL acts as a transducer. In other words, it is in and through this layer DL, that the impacting photons generate the electrical signals. Specifically, the conversion layer is sandwiched between pairs of electrodes EL. Only the anodes are shown in the sectional view of FIG. 2, arranged at the distal face of the conversion layer DL. The electrodes EL are spaced discretely apart at a certain D distance and in a pattern on the distal surface of the direct conversion layer DL. Each electrode EL has a native size (effectively an area) d. The size may also be expressed as pitch. The electrodes EL define a "pixelation" of the otherwise unstructured conversion layer DL. Each electrode EL corresponds to one detector pixel, only three pixels PX1-3 being exemplary shown from the whole array of pixels. The electrodes EL are sometimes referred to herein as "pixels" in short. The electrodes EL may be arranged as a layer of TFTs (thin-field-transistors). A voltage is applied across the electrodes and the direct conversion layer DL. Typically, the cathode is not pixelated to apply the same voltage across the layer DL. X-ray photons Xph impact on crystals in the detector layer DL. Depending on the photon's Xph energy, a number of electrons and holes are released that are otherwise bound in the crystal. The so released electrons and holes may themselves release further electrons and holes, and so on. Due to the applied voltage, a main part of the electrons and the holes cannot recombine and form respective charge clouds CC. Driven by the applied voltage, the electron charge cloud CC drifts (in the view of FIG. 2, downwardly) towards the anodes EL to cause the earlier mentioned electrical signals, specifically electrical pulses. The electrical signals are then processed by the DAS.

Each count of a photon energy represents an event. Much of the event counting capability of the imager, and its fidelity, rests on its ability to distinguish between charge clouds caused by different photons. So, ideally, each electrode pair EL would respond to a charge cloud of a single photon at a time. Unfortunately, this is not always happening because of a non-negligible finite size of the charge clouds. In case the charge cloud is generated between adjacent pixels EL (as shown in FIG. 2), one fraction of the cloud can be directed by the corresponding electrical field to one of said pixels and another fraction is directed to another pixel(s). In other words, the ensuing cloud charge CC may be registered by two or more, in particular adjacent, electrodes. This undesirable effect is called "charge sharing". In other words, the cloud charge CC induced by a single photon Xph through interaction with the direct conversion layer is shared between two or more anodes/pixels. This charge sharing may cause double or multiple counts for a single given photon because the charge is shared among two or more of the pixels that are defined by the anodes. Charge sharing may therefore disturb the energy discrimination capability of the imager XI and, ultimately, the fidelity of the imagery.

It will be understood, that the above described architecture of the detector module XD is purely exemplary and for the purpose to illustrate the signal chain from the X-ray photons Xph to the electrical signals in the context of charge sharing. Numerous other modifications to the above described design in FIG. 2 are also envisaged herein. In particular, detector modules XD of the indirect conversion type that include, instead of layer DL, a scintillator layer and, coupled thereto, a photodiode layer, are also envisaged herein in the alternative. In case of the indirect conversion type, the pixilation is given at least partly by the crystal growth in the scintillator or mechanical structuring.

Figure 3:
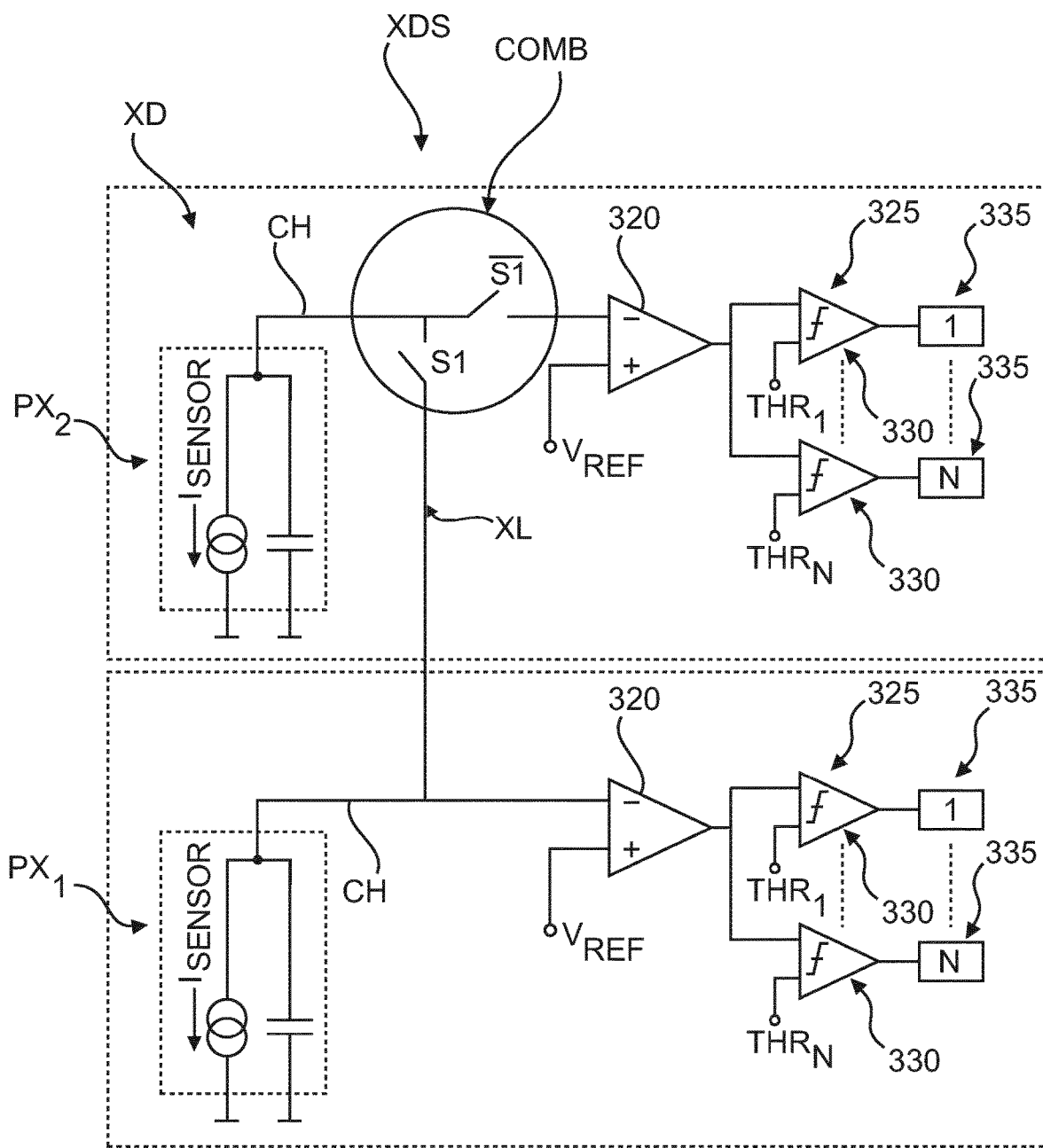
FIG. 3 shows a schematic circuitry diagram of an X-ray data acquisition system according to a first embodiment.

Reference is now made to FIG. 3, which shows more details of the readout circuitry of the DAS as envisaged herein according to one embodiment. The left part shows exemplary. the detector pixels. For clarity, only two pixels PX1,PX2 are shown.

The pixels PX1,PX2 produce electrical (current) pulses having a magnitude ("height") with its area corresponding largely to the energy of the impacting photons Xph. A height of the electric pulse detected at a given pixel PX1,PX2 is a function of the impacting photon's Xph energy. The higher the photon energy, the higher the pulse magnitude that can be detected at the respective pixel PX1,PX2.

Each pixel electrode PX1,PX2 is coupled by an individual raw signal line (or "(pixel) readout channel") CH with photon counting circuitry of the DAS.

According to one embodiment, the electrical pulses generated at the pixels PX1,PX2 are processed by the photon counting circuitry in the following manner: Optional conditioning circuitry includes a pre-amplifier 320 amplifies each electrical signal generated by any of pixels 218.

The optional conditioning circuitry may further include a pulse shaper (not shown) to processes the amplified electrical signal for a detected photon and to generate a corresponding analog signal that includes a pulse height such as a voltage/current or other pulse indicative of a detected photon. The so generated pulse has a predefined shape or profile. In this example, the pulse has peak amplitude that is indicative of the energy of the detected photon.

An energy-discriminator 325 energy-discriminates the analog pulse. In this example, the energy discriminator 325 includes a plurality of comparators 330 that respectively compare the amplitude of the analog signal with a respective threshold that corresponds to a particular energy level. Neighboring threshold define an energy bin. Said differently, discriminator 325 operates to determine "height" of the incoming pulses as generated by shaper. More specifically, each comparator 330 produces an output count signal that is indicative of whether the amplitude of the pulse exceeds its threshold. In this example, the output signal from each comparator produces a digital signal that includes a transition from low to high (or high to low) when the pulse amplitude increases and crosses its threshold, and from high to low (or low to high) when the pulse amplitude decreases and crosses its threshold.

In an exemplary comparator embodiment, the output of each comparator transitions from low to high when the amplitude increases and crosses its threshold and from high to low when the pulse amplitude decreases and crosses its threshold.

A counter 335 counts the rising (or in some embodiments the falling) edges respectively for each threshold. The counter 335 may include a single counter or individual subcounters for each threshold. Optionally, in case of two-sided bins only, there is an energy binner (not shown) that energybins or assigns the counts into energy ranges or bins corresponding to ranges between the energy thresholds. In fact, in the preferred embodiment with high flux, there is no binning operation into ranges but it is purely the counts of threshold crossings (ie, one-sided binning) that are being registered.

The count data (denoted herein as M, as described in more detail further below) may then be used to energy-resolve the detected photons. Said differently, the photon counting circuitry of the DAS operates to quantize the pulse height of each incoming pulse from each pixel PX1,PX2 into the energy bins defined by the number of voltage thresholds. K (K≥2) (voltage, amperage or other physical quantity indicative of energy) thresholds are capable of defining, K different energy bins for recording pulse heights higher than respective ones of said threshold. For instance, a pulse whose edge rises beyond (that is "crosses") two of said thresholds will elicit a count for each of the two bins associated with the respective two thresholds. If only the lower one of the threshold is crossed, there will be only one count, etc. But this is an example only as in some embodiments only falling edges elicit counts or both, rising and falling edges elicit counts.

The photon counting circuitry furnishes at its output, for each pixel PX1, PX2, a number of counts in each bin as recorded in unit time. These photon count rates per bin and pixel forms projective photon counting data, which may be formally written as $M=(m_1, \ldots, m_K)^i$, with vectors of count rates $m_k$, whilst i denotes the respective pixel and $1 \leq k \leq N$ the number of energy bins used. Said differently, $m_k$ denotes the number of times (counts) per unit time that a pulse, whose height falls into bin k, has been recorded at pixel i. The counts may be normalized by the frame rate to represent the count rates, that is, counts per unit time. Normalization however is not a necessity and the proposed system may also operate on non-normalized count data. There are 2, 3 or more energy thresholds. In rotational systems such CT or C-arm, the recorded count rates may be different for different projection directions so the above notion may be supplemented with an additional index for the projection direction. In this later case, M forms a sinogram in the CT embodiment.

The so quantized event count data M may then be processed by the image processor IP.

Figure 4:
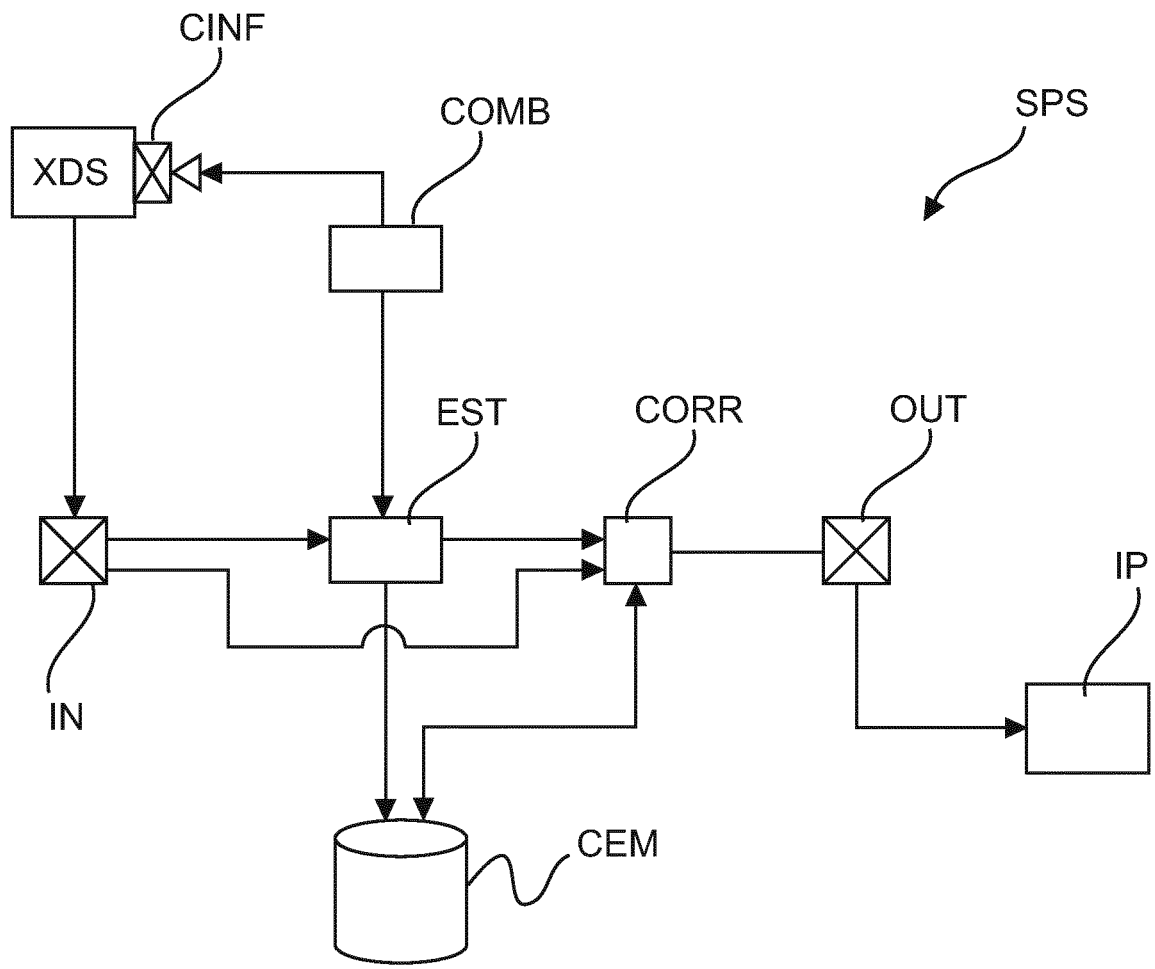
FIG. 4 shows a schematic block diagram of a signal processing system for charge sharing estimation.

Reference is now made to FIG. 4, which shows a schematic block diagram of the signal processing system SPS configured for charge sharing correction of data generated in or by the detector sub-system XDS during operation of imager XI.

The X-ray detector sub-system XDS is configured to be operable in multiple detector configurations. Data generated in a calibration exposure by the sub-system XDS in the different detector configurations can then be compared to assess or quantify the charge sharing effect. A detector configuration is defined by the pixel size PX of the detector unit XD. One such size, the native size d, of the detector pixel is given by the hardware arrangement that gives rise to the pixilation as explained above in FIG. 2. The pixel size D may be given by the size of the electrodes in the read-out layer as explained above at FIG. 2 for the case of the direct conversion detector. Alternatively, the native size may be given by the crystal growth in the scintillation layer and/or the size of the photon detectors used in the case of an indirect conversion. In short, the native pixel size is the smallest possible at which the imager can operate to provide the best spatial resolution. The native pixel size d is the smallest physical arrangement in the detector unit that converts X-ray into electrical pulses.

A pixel size for a different detector configuration may be achieved by combining (eg, by binning) the detector signals in relation to multiple of such native pixels to realize a different detector configuration and hence a different (virtual or effective) pixel size. For instance, data signals in relation to four native pixels may be combined to so realize a "virtual" detector pixel with size four times the native pixel size d. Such a configuration may be referred to as "P-to-1", that is, there are P native pixels to one virtual pixel, with P being a natural number larger than 1. Specifically, practical values for P include 2, 3, 4 or even larger such as 8 or even all the way up into two-digit figures. For clarity, using P=1, results, in this notation, in "1-to-1", which is the configuration that corresponds to the usual native pixel size p configuration. The different detector configuration may be realized by a signal combiner functionality COMB.

Referring back to circuitry in FIG. 3, this shows such a combiner functionality COMB according to one embodiment, integrated into the X-ray sub-system XDS, in particular into the photon counting circuitry of the X-ray sub-system XDS. Specifically, the combiner COMB is realized as a binner that bins two pixels PX1 and PX2 into a single channel to produce a 2-to-1 detector configuration, thereby reducing spatial resolution by half. To this end, combiner COMB includes switches $S1, S2=\overline{S1}$ as indicated in FIG. 3. The switches are arranged to pick up and combine electrical pulses travelling down readout channel CH, with "—" denoting the negation operator relative to the two states "open (off)", "closed (on)" of switch S1. S1 is arranged on a cross link line XL between the two readout lines for PX1,PX2. Specifically, switch S1, when switched from open to close, will cause switch S2 (eg, arranged on readout line of PX2) to disconnect pixel P2 from its native pitch readout channel CH and connect it to the input node corresponding to the readout electronics of pixel P1. Pulse signals generated on either pixel PX1,PX2 will be summed by superposition and are now on a single readout channel (eg, that of pixel PX1) and processed by the photon counting circuitry of pixel PX1. It will be appreciated that charge sharing events across PX1 and PX2 (simultaneous in time) will be added and treated as one single event at the right deposited energy at thresholder 325 and discriminator 330 for pixel PX1.

Figure 5:
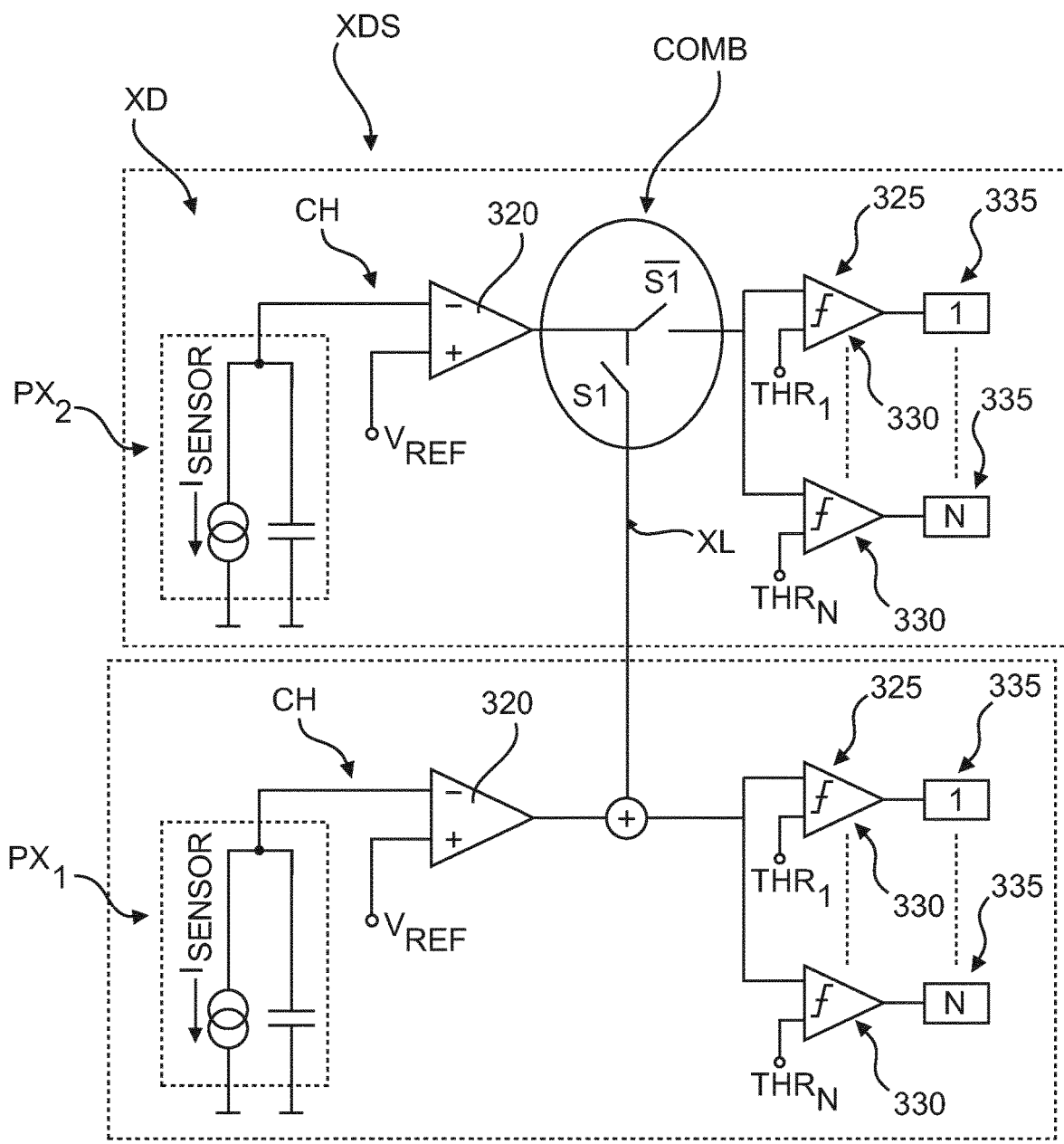
FIG. 5 shows a schematic circuitry diagram of an X-ray data acquisition system according to a second embodiment.

FIG. 5 shows an alternative combiner COMB arrangement for binning, where the combiner functionality COMB is integrated into a different stage of the photon counting circuitry. Whilst in FIG. 3 the combiner acts on the read-out signal line CH to pick-up and combine pulses, in FIG. 5 the combiner COMB is arranged instead downstream and forms the combined signals at the output stage of the amplifier 320 or the shaper. That is, the charge pulse signals are not combined in themselves, but rather the outputs of the respective shapers are so combined. S1 is now arranged on a feedline from the shaper/pre-amplifier 320 to the respective discriminator 325, whilst S2 is arranged on a respective cross-line line X1 between the feedlines.

Alternatively, the combiner functionality COMB may be integrated in other stages of the DAS, in particular in other stages of the photon counting circuitry, for instance at the pulse counters 335 themselves. This combiner embodiment may then involve calculating a resulting equivalent energy as one may not simply add counts as such when combining, but instead the combining operation may be effected by the system incrementing the count by 1 in the bin for the higher threshold, based on the resulting equivalent energy.

In terms of robustness to the quadratic sum of noise contributions, the embodiment in FIG. 3 is more favorable than the one in FIG. 5, because in FIG. 3 the noise from all binned readout electronics is combined into one single node. As used herein then, the term "detector signal" may relate to any pulse or combined pulses irrespective of where in the detector sub-system XDS these are picked up, whether at the readout lines CH (such as in FIG. 3) or at other stages downstream, such as in the embodiment of FIG. 5. Although the particular embodiments in FIGS. 3, 5 of the combiner COMB are configured to produce 2-to-1 configurations it will be understood that the concepts can be extended to several other configurations, for any P>2, e.g., 3-to-1, 4-to-1, 5-to-1, etc. That is, the switches may be operated to add up not only two pulses but more than two, such as 3, 4 or 5 or more, and any sub-sums thereof. For instance, an arrangement for, say, 5-to-1, can form pulse sums made up from 5 pulses from 5 different pixels and preferably each sub-sum of less than 5 pulses for any selection k from the 5 pulses. In other words, the switch network at the input node may be made and controlled by a suitable logic such that multiple detector configurations are implemented, thus allowing to obtain at least 2 different detector configurations for any selection of k, with $1<k\leq P$ to produce any one of P different configurations P-to-1. One way to implement such a network is to add cross link lines XL between some or all (or at least P) pixel readout lines, with respective switches on each cross link line, and a switch on each (of the P) pixel readout lines CH. This network may be reduced in complexity by a Karnaugh-Veitch diagram analysis or by other tools from digital synthesis.

A single combiner COMB (comprising the two switches S1,S2) for the whole detector XD may be enough as shown in FIGS. 3,5, but preferably more such similar combiners with respective switches S1,S2 are arranged between a plurality of pixels, respectively, and not merely for two PX1,PX2 pixels as shown. In particular and preferably, for any two neighboring pixels there is a combiner COMB similar or like the one exemplary shown in FIGS. 3,5. For instance, a further such combiner (not shown) is arranged between pixel PX3 (not shown) to combine with pulses from PX2, and so on.

Not all detector configurations may be desirable for each imaging setup, so the combiner may not be universal but may be pre-configured to the specifics of the imager XI at hand. For example, in a CT setup with native pixel pitch D 500 μm and an anti-scatter grid with 1 mm pitch, the combiner may be constrained to, say, a 2-1 and 4-1 configuration within the ASG's walls. To this end, the combiner may not need to be configurable for combinations that go beyond a group of native pixels confined within the area between two neighboring ASG walls. Thus, the combiner may be configured (eg, hardwired) for a fixed and limited number of different (at least two) detector configurations. However, user configurable combiners that are capable to be configured for all possible configurations up to and including a given P are also envisaged herein in other embodiments.

It will be understood that the implementation of each combiner functionality COMB in terms of the negated pair of switches $S1,S2=\overline{S1}$ is merely one embodiment from other embodiments equally envisaged herein in alternatives. The switch-pair embodiment is however a preferred embodiment due to its simplicity, reliability. The types of switches envisaged herein include for instance a transistor, such as a metal-oxide-semiconductor field-effect transistor (MOSFET) with low series resistance when in "on"-state and low leakage when in an "off"-state.

Referring back to FIG. 4, the signal processing circuitry SPS includes suitable interface means CINF and related controllers through which the SPS can request the X-ray detector system XDS to operate at least two of desired ones of different detector configurations. In this manner respective calibration data MDC1 and MDC2 can be generated for the respective detector configurations, denoted herein as DC1 and DC2. "DC1" is used herein to denote the native pixel size detector configuration. As mentioned above, the number of pixels N to be combined together is user configurable. Furthermore, it is not necessary to perform the calibration for each and every pixel of the detector array XD, but it may be sufficient to conduct this for a single group of pixels (anywhere on the detector array XD) that has the desired number of pixels (two or more such as three or four or more). Taking a measurement for only a subset of pixels allows reducing the amount of data to be processed. After the X-ray detection system XDS has been operated in the two or more detector configurations, the respective calibration data and MDC1 and MDC2 is received at input port IN of the signal processing system SPS.

An estimator EST then uses the (at least) two data sets MDC1 and MDC2 to estimate or quantify the charge sharing. In one embodiment, a functional model is used by the estimator EST to estimate the charge sharing impact in form of correction values C. These correction values are in particular associated with the detector configuration DC1 of the smaller pixel size as this is expected to be more affected by charge sharing.

One way to estimate of the charge-sharing impact fs by forming ratios from detector signals respectively generated for the two detector configurations. For instance, for P-to-1 configurations (P a natural number ≥2), ratios may be formed as per $$C=P*MDC1/MDC2 \text{ or } MDC2/P*MDC1, \quad (1)$$

with MDC1 being the detector signals for the native sized configuration and MDC2 being the combined signal for the configuration with P times the native size p. For instance, if detector signals in relation to P pixels (eg. P=4) are combined, this value will differ due to charge sharing from the value obtained by taking P times the detector signals in the configuration DC1 of the smaller pixel. The ratio C will hence differ from unity. The ratio C as per the above can thus can be used as a correction factor to be applied to detector readings when the detector is operated as usual (without using the combiner) at the detector configuration DC1 of the smaller pixel size. Forming, for estimation purposes, functional expressions other than ratios is also envisaged herein, such as weighted or absolute differences, as will be explained in more detail further below in relation to FIG. 6. It should be noted that ratio C is in general formed for each respective counts for each bin of counter 335. In other words, the ratios C are formed for each energy bin.

For obtaining the two data sets MDC1, MDC2, a user or by a random generator, a single pixel, say PX1, is specified. The specification can be achieved for instance by selecting a coordinate of the pixel PX1. Each pixel is addressable by a unique coordinate. For instance, the pixel pattern may be rectangular with the pixels being arranged in rows and columns. Each pixel has then a unique coordinate (x,y), x being its row and y its column. Other addressing schemes may also be used. In addition, a group of two or more pixels is selected, preferably in a neighborhood around the pixel PX1. For instance, in a grid like arrangement of the pixel array XD, the P=4 adjacent pixels around pixel PX1 are so selected.

The detector, and hence the group of pixels along with pixel PX1, is then exposed to radiation by operating the X-ray source in a calibration phase. Two measurements are then taken, one for each of the configuration, e.g. one for the native size (DC1) and one for the larger pixel size configuration, P-to-1 (eg, P=4) DC2. More than 2 exposures are required if more than 2 detector configurations are used. In the exposure for the DC2 configuration, the combiner COMB operates to combine the detector signals in relation the groups of pixels and pixel PX1 to form the two data sets, MDC1, MDC2. As a result, two data sets MDC1, MD2 are obtained in the calibration phase. Data set MDC1 includes the (usual) detector signal as recorded by counter 335 as counts across the bins for pixel PX1 whilst the other data set MDC2 includes the combined signals from for the P=4 pixels in the group, as recorded as counts in bins of counter 335. So, in principle, for each energy bin, each data set MDC2, MDC1 comprises a single number, and these number can be used to estimate the charge sharing impact as per C in eq (1) above, with P=4. Other values for P, such as 2, 3, 5 or more may be used instead.

This same correction factors C may be used for all other pixels during the actual imaging phase (after the above described calibration phase) to correct for charge sharing. Alternatively, and preferably, the above is repeated for a plurality of different pixel positions $PX_j$ (in particular for all pixels in the array XD) and the respective correction factors Cj are then averaged or otherwise arithmetically combined.

Alternatively, and more preferable still, correction factors Cj are retained pixelwisely, dedicated to each respective pixel j, and the collection of correction factors are stored in memory CEM, each in association with the respective pixel location j. The correction operation then includes a look-up operation to retrieve the associated correction factor $C_j$ for each pixel $PX_j$ during or after imaging.

Preferably, and to obtain better results, the above procedure for obtaining the calibration measurement MDC1, MDC2 are obtained in the context of an energy calibration and/or material calibration (more on this further below at FIG. 7), and/or of different ranges of impinging X-ray flux. The data sets MDC1,MDC2 form a multi-dimensional collection of numbers, indexed by the respective bin (that is the energy), and at least by material type/thickness. I addition and optionally, indexing by flux ranges, or other parameters may be used. As a consequence, the correction data C is likewise a multidimensional array of numbers, with entries associated through suitable indexing with the respective pixel, bin, material, energy, etc or other relevant factor.

Next, in imaging mode, after the above described calibration mode, detector signals (in relation to the actual object OB to be imaged) are then received at the input port IN from the X-ray detector sub-system XDS. In imaging mode, no calibration is required, and the object OB detector signals are then directly passed on to the corrector CORR.

The corrector CORR then retrieves the associated correction values $C_j$ stored in memory CEM and associated with the detector configuration (eg, DC1) used for the current imaging. The corrector then applies (for instance, multiplies) the correction values $C_j$ to the received object OB detector signals and forms corrected detector values which are then output at output port OUT.

The so corrected detector signals can then be used by the image processor IP to compute the desired imagery such as transmission, phase contrast, dark field or spectral image or other.

As can be appreciated from the above described, the charge sharing impact assessment on data generated by the sub-system XDS may be tailored to a specific imaging apparatus XI, to a specific detector unit XD, to specific pixel portions of a detector unit XD, even down to individual pixel level. The proposed sub-system may be retrofitted to existing imagers XI.

Figure 6:
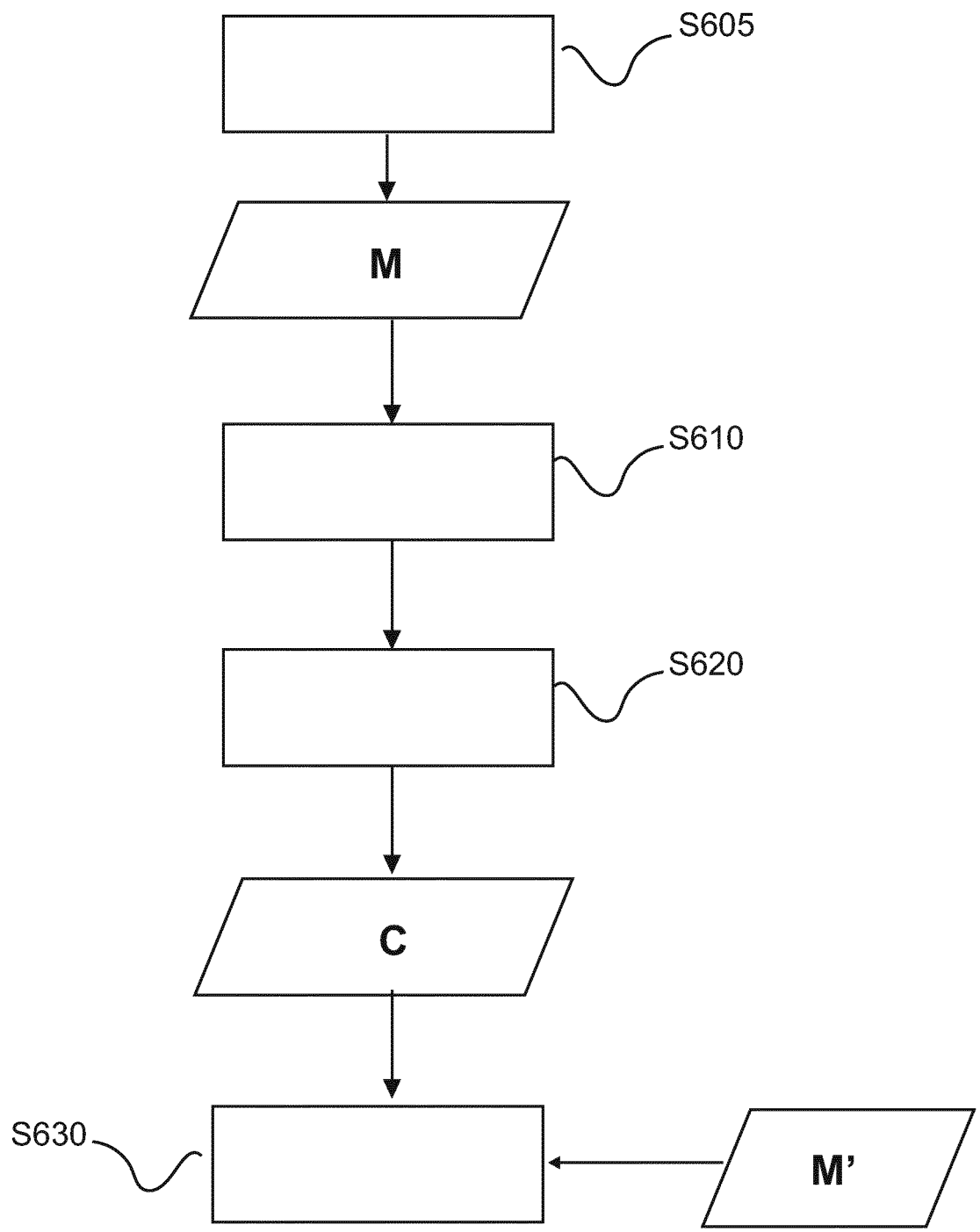
FIG. 6 shows a flow chart of a signal processing method.
Figure 7:
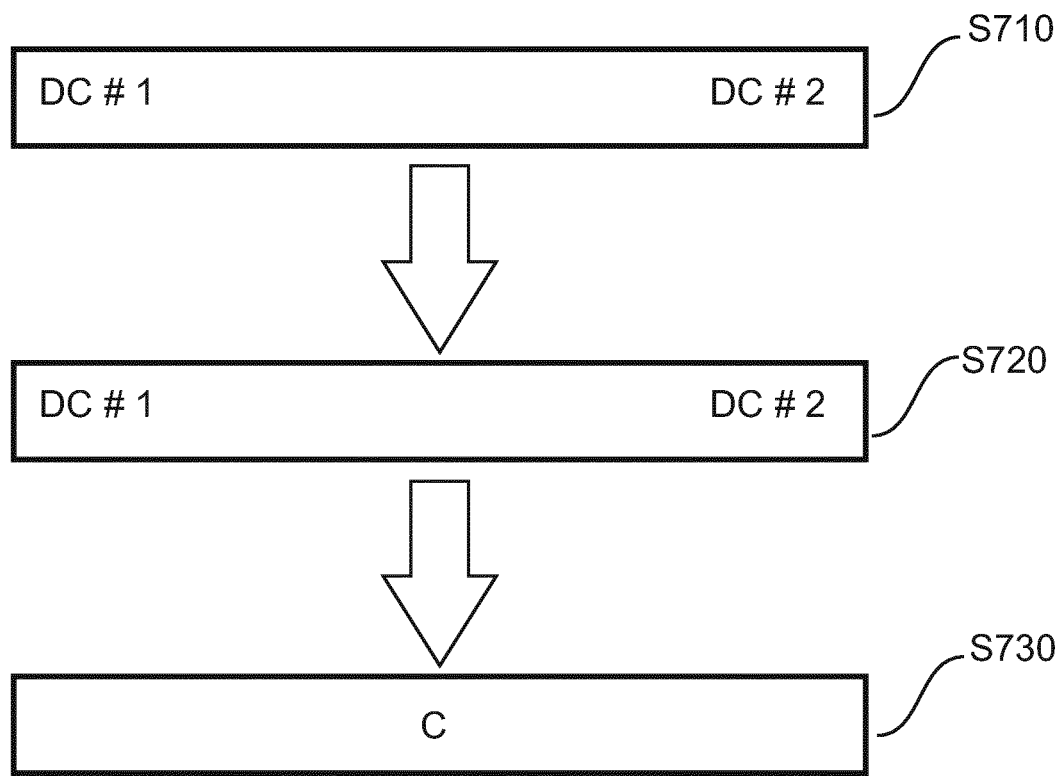
FIG. 7 shows a flow chart for a method step of obtaining calibration data.

Reference is now made to the flow chart at FIGS. 6, 7 to explain in more detail operation of the signal processing system SPS. However, it will be understood that the method steps to be described below are not necessarily tied to the architecture as per FIGS. 1-5. In particular, the method steps explained in the following may also be understood to constitute a teaching in their own right.

Turning first to FIG. 6, at preliminary step S605 (two or more) respective data sets (calibration measurements" or calibration data) are acquired in a calibration run for respective different detector configurations. Each configuration is determined by the pixel size used, and the pixel size is different for each set. The different calibration measurements M=(MDC1, MDC2) can be obtained by the combiner circuitry COMB that combines, in particular sums, detector signals in relation to different pixels PX1, PX2. The combination may occur at any stage of the X-ray detector sub-system XDS. In particular, the combination may occur in the analogue stage or once the signals are digitized by the counter stage. The combiner operation results in different counts (which form the data sets M) by the photon counting circuitry as per the two different configurations, and it is these counts that are designated herein as calibration measurements ("calibration data") M=(MDC1, MDC2).

Preferably, one of the two or more detector configurations is set at the smallest possible, that is the native pixel size, while the other is chosen as a suitable multiple P thereof such as two or four or 8 times the native configuration, but in principle P may be any number larger than 2 is earlier mentioned. This native detector configuration is denoted herein by DC1, with MDC1 denoting the associated calibration measurements.

At step S610 the two (or more) calibration sets MDC1 and MDC2 are then received at a data processing unit PU, such as a computer unit of a work station or a computing functionality integrated into the imager XI.

At step S620 an estimate of charge sharing impact is computed. This estimation or quantification of the charge sharing impact may be expressed as correction data such as correction values or factors. In the estimation, a functional model f is used to combine the measurements for the two (or more) different detector configurations DC1, DC2.

In general, given a functional model f, the correction data is:

$$C_b = f(MDC1_b, MDC2_b) \qquad (2)$$

The index "b" differentiates the counts $MDC1_b$, $MDC2_b$ in the various energy bins b for the (at least two) different detector configurations DC1, DC2.

One functional model f is linear dependence which leads to the ratios earlier mentioned at (1), so in this case f is:

$$C_b = f(MDC1_b, MDC2_b) = \frac{MDC2_b}{m * MDC1_b} \qquad (3)$$

In another embodiment, an additive functional model is used, such as:

$$C_b = f(MDC1_b, MDC2_b) = (m*MDC1_b - MDC2_b)^k, \text{ with } k \geq 1 \qquad (4)$$

In (4), if there was no charge sharing, C would reduce to zero, and any deviation therefrom may be used as an indication of the amount of charge sharing particular. The, if k=1, the difference may be taken as the absolute of signed sum. The square deviation k=2 may also be used with benefit.

Although in the above, main reference has been made to using two detector configurations DC1, DC1 and related calibration data M=(MDC1, MDC2), the method may also be extended by taking three or more (p>2) data sets at three or more detector configurations and by compiling this information to extract therefrom correction data and estimates for the charge sharing. For instance, the functional model may include forming more complex ratios or (weighted sums). That is, more than two detector configurations p (such as three, four or more) may be functionally and arithmetically combined as per $$f(MDC1_b, MDC2_b, \ldots, MDCp_b) \quad (5)$$

to quantify the charge sharing impact. For instance, one may process data $MDC_j$, $MDC_k$ for any two configurations j,k out of n configurations (of which there are (of which there are $\binom{p}{2}$)

and form ratios as per the above for any pair j,k. The $$\binom{p}{2}$$

ratios are then averaged (weighted or mean) to so arrive at the correction factors C.

As a further extension to what has been said above, it may not always be necessary to take one of the configurations as the native detector pixel size configuration. For instance, one configuration may be formed as comprising groups of pixels larger than 1 whilst the second (third, etc) configuration also relates to groups of a different size. In other words, P-to-L configurations, with L larger than 1, may also be considered if the situation asks for a down-sampling of the imaging task.

The above quantification at eqs (1), (3) of the charge sharing impact in terms of ratios has been found to be a good approximation for low flux settings. However, in higher flux settings the above linearization at eqs (1), (3) can be refined by modulation with an exponential term to so model the influence of high flux and the connection with the detector electronics in particular, the dead time and/or paralyzeability. In particular, expression (3) may be refined into:

$$C_b = f(MDC1_b, MDC2_b) = \frac{MDC2_b}{m * MDC1_b} * e^{k*v*\tau} \quad (6)$$

where k is a constant less than 1 (eg, ¾) v is the is the flux of the larger pixel DC2, and τ is a deadtime of the detector system XDS.

The above relationships at any one of models in eqs (1)-(6) can be further refined by including one or more further terms that represent a pulse pile-up model.

In the previous estimation embodiments (eqs (1)-(6)), it is assumed that binning of two or more pixels has no impact on a transient response of the direct conversion material. This can be considered a good approximation for moderate binning configurations (e.g. 4×500 μm-to-linin in a 4-to-1 configuration). For large equivalent pixels, e.g. 8-to-1, a significant change in transient response may occur (e.g., longer transient responses for large pixel configuration) due to different weighting potential profiles (large pixels may not benefit from the so-called small-pixel effect). Such different transient responses might impact the signal generation of the pre-amplifier 320 or similar components of the front-end electronics in the DAS. One example of such an impact due to different transient responses is. ballistic deficit. To this end, it might be required that for each detector configurations, a different energy calibration is used to achieve comparable results.

At step S630 the estimate, in particular the correction data C, can then be used to correct, for charge sharing, detector data M' generated by the imager XI during an imaging operation in which the object OB is imaged. The imaging operation is preferably one in which the employed detector configuration corresponds to the small pixel size configuration DC1 earlier used in the calibration phase. In other words, the correction data C as per (1) and (3) is preferably associated with configuration DC1, so (1), (3) may be written in terms of $C^{DC1}$ to better indicate this dependence notationally. However, using the inverse, $C^{-1}$, of the correction data may also be used to correct data obtained when operating imager XI at configuration DC2 with the larger pixel size.

The correction data is either applied directly during imaging (this is preferable), or, alternatively, the (as yet) uncorrected detector readings M' in relation to the imaged object OB are first stored or buffered, and the correction data C is applied at a later stage, for instance when visualization is requested. Depending on which functional model is used in step S620, the correction can be effect by multiplying (eq (1)) or subtracting or adding (eq (4)) the correction values with, from or to the image data M'.

Although the above described method could be performed by simply exposing the X-ray detector during an air scan with radiation, it is preferably to collect the calibration data in the context of energy and material calibration schemes. This is explained in more detail in the flow chart in FIG. 7 to which reference is now made. In other words, the flow chart in FIG. 7 provides more details on how to perform the method step S605 of producing the two or more sets of calibration data.

At step S710, an energy calibration is performed so that all pixel thresholds in the discriminator 325 a set to identical energies throughout the detector array XD. In particular, the energy calibration allows factoring in gain and offset.

In this calibrated state of the detector (sub)system, a material calibration is performed at step S710, with a certain configuration of calibration materials c in the beam XB. Suitable materials ("phantoms") are any one of Water, Delrin, Tin, Teflon, or k-edge materials (such as AU, Bi, Pb), or others. The material should have at least two different thicknesses. One exposure may then be enough, or otherwise multiple items of said material are stacked up to realize different thicknesses and two more exposers may need to be run. The material calibration allows configuring a curve or look-up table (LUT) to translate count rate into material thickness for imaging. The more material thicknesses are used, the more accurate the LUT. For a given count rate, an associated thickness may then be interpolated form the LUT.

The corresponding calibration data for the first detector configuration DC1 (the native one) will be denoted by $MDC1_{c,b}$, where the index c differentiates calibration materials (or thickness) c in the beam.

Similarly after switching the detector configuration by binning as described above, the energy calibration and the material calibration are repeated at step S730, with the corresponding measurement result $MDC2_{c,b}$. Since the measurements $MDC1_{c,b}$ and $MDC2_{c,b}$ correspond to exactly the same irradiation conditions, there exists the assumed relation f (as explained above) between them influenced by the amount of charge sharing. Optionally, in further step, measurements may be obtained for a range of different flux-settings, with the correction C further indexed by flux rate.

The above procedure in steps S710-730 illustrates the above mentioned multi-dimensional nature in the most general case of the correction data C, due to the various dependencies on b,c, pixel position (x,y), detector configuration $DC_j$. However, in some instances with due simplifications, the dependencies may be reduced to the bin dependency.

The components of the image processing system SPS may be implemented as software modules or routines in a single software suit and run on a general purpose computing unit PU such as a workstation associated with the imager XI or on a server computer associated with a group of imagers. Alternatively, the components of the image processing system ISP may be arranged in a distributed architecture and/or "Cloud" and connected in a suitable communication network.

As a further alternative, some or all components of the SPS may be arranged in hardware, such as a suitably programmed FPGA (field-programmable-gate-array), or as hardwired IC chip such as an ASIC (application-specific integrated circuit), on a PCB module included into the circuitry for the detector sub-system XDS.

Although in the above, the convertor converts into effective material path length e, this should be considered broadly, as converting into any other parameter that is equivalent to said effective path length is also envisaged herein. Furthermore, in relation to any of the above mentioned formulae, mathematically equivalent re-formulations of these are also envisaged herein.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging arrangement, comprising:
    an X-ray imaging apparatus comprising a detector sub-system, the detector sub-system having a native pixel size;
    a signal processing system comprising:
        a combiner configured to combine signals generated at the detector sub-system in response to X-radiation exposure and obtain at least one of a first data set and a second data set, wherein a pixel size in one of the first and second data sets is the native pixel size and in the other data set is a multiple of the said native pixel size;
        an estimator configured to compute, based on the two data sets, an estimate of a charge sharing impact by functional model comprising a correction factor; and
        a corrector configured to correct, for the charge sharing impact and based on the estimate, a third data set generated by the detector-subsystem or another detector.

2. The imaging arrangement of claim 1, wherein the combiner includes binning circuitry to bin the signals generated at the X-ray detector sub-system.

3. The imaging arrangement as per claim 1, wherein the estimator is configured to form the correction factor by forming one or more ratios based on values as per the first and second data set to obtain said estimate.

4. The imaging arrangement as per claim 1, wherein the detector sub-system is an energy resolving type.

5. A signal processing method, comprising:
   combining signals generated by a detector sub-system having a native pixel size in response to X-radiation exposure, to obtain at least one of a first data set and a second data set, wherein a pixel size in one of the first and second data sets is the native pixel size and in the other data set is a multiple of the said native pixel size;
   computing, based on the two data sets, an estimate of a charge sharing impact impact by means of a functional model comprising a correction factor; and
   based on the estimate, correcting, for the charge sharing impact, a third data set generated by the detector sub-system or by another detector sub-system.

6. A non-transitory computer-readable medium having executable instructions stored thereon which, when executed by at least one processor, cause the at least one processor to perform a signal processing method comprising:
   combining signals generated by a detector sub-system) having a native pixel size in response to X-radiation exposure, to obtain at least one of a first data set and a second data set, wherein a pixel size in one of the first and second data sets is the native pixel size and in the other data set is a multiple of the said native pixel size;
   computing, based on the two data sets, an estimate of a charge sharing impact impact by means of a functional model comprising a correction factor; and
   based on the estimate, correcting, for the charge sharing impact, a third data set generated by the detector sub-system or by another detector sub-system.

* * * * *